United States Patent [19]
Schleinz et al.

[11] Patent Number: 5,458,590
[45] Date of Patent: Oct. 17, 1995

[54] INK-PRINTED, LOW BASIS WEIGHT NONWOVEN FIBROUS WEBS AND METHOD

[75] Inventors: Robert J. Schleinz, Appleton, Wis.; Steven W. Fitting, Acworth, Ga.; Joseph S. Kucherovsky, Philadelphia, Pa.; Daniel J. Conrad, Murfreesboro, Tenn.

[73] Assignee: Kimberly-Clark Corporation, Neenah, Wis.

[21] Appl. No.: 338,986

[22] Filed: Nov. 14, 1994

Related U.S. Application Data

[63] Continuation of Ser. No. 171,309, Dec. 20, 1993, abandoned.

[51] Int. Cl.[6] .................................................... A61F 13/15
[52] U.S. Cl. ...................... 604/361; 604/385.1; 101/483
[58] Field of Search ............................ 106/202; 101/483, 101/170, 450.1; 604/361, 385

[56] References Cited

U.S. PATENT DOCUMENTS

| | | | |
|---|---|---|---|
| 3,732,139 | 5/1973 | Fechillas | 161/170 |
| 3,867,171 | 2/1975 | Ellsworth | 117/38 |
| 4,022,211 | 5/1977 | Timmons et al. | 604/361 |
| 4,036,136 | 7/1977 | Takagi | 101/483 |
| 4,041,203 | 8/1977 | Brock et al. | 428/157 |
| 4,423,676 | 1/1984 | Neel | 101/211 |
| 4,437,408 | 3/1984 | Arkans | 101/483 |
| 4,530,874 | 7/1985 | Hendrix et al. | 428/266 |
| 4,574,732 | 3/1986 | Verwey et al. | 118/642 |
| 4,610,920 | 9/1986 | Mudge et al. | 428/288 |
| 4,646,362 | 3/1987 | Heran et al. | 2/400 |
| 4,713,068 | 12/1987 | Wang et al. | 604/366 |
| 4,713,069 | 12/1987 | Wang et al. | 604/378 |
| 4,758,239 | 7/1988 | Yeo et al. | 604/366 |
| 4,766,840 | 8/1988 | Beckley et al. | 118/46 |
| 4,796,556 | 1/1989 | Bird | 118/46 |
| 4,818,600 | 4/1989 | Braun et al. | 428/290 |
| 4,828,556 | 5/1989 | Braun et al. | 604/365 |
| 4,841,903 | 6/1989 | Bird | 118/46 |
| 4,844,952 | 7/1989 | Korenkiewicz et al. | 427/258 |
| 4,939,992 | 7/1990 | Bird | 101/183 |
| 4,940,464 | 7/1990 | Van Gompel et al. | 604/396 |
| 5,163,247 | 11/1992 | Weber et al. | 47/9 |

FOREIGN PATENT DOCUMENTS

0442673A1  8/1991  European Pat. Off. .

OTHER PUBLICATIONS

AATCC Test Method 116–1983.
AATCC Test Method 8–1972.
AATCC Test Method 153–1985.
AATCC Test Method Evaluation Procedure 1.
AATCC Test Method Evaluation Procedure 2.
AATCC Test Method Evaluation Procedure 3.

*Primary Examiner*—Jerome L. Kruter
*Attorney, Agent, or Firm*—Douglas L. Miller; Kimberly-Clark Corporation

[57] ABSTRACT

Low basis weight nonwoven fibrous web, which can be incorporated into personal care articles, has an ink printed thereon and has an average wet crockfastness value of at least about 4 or greater. A method is provided for making the ink-printed web.

28 Claims, 1 Drawing Sheet

INK-PRINTED, LOW BASIS WEIGHT NONWOVEN FIBROUS WEBS AND METHOD

This is a continuation of application Ser. No. 08/171,309 filed Dec. 20, 1993, now abandoned.

BACKGROUND OF THE INVENTION

The present invention is directed to the printing of nonwoven webs and the webs printed thereby. Specifically, the printed nonwoven webs are polyolefin fibrous webs printed with an ink exhibiting improved adhesion to the webs.

The printing of substrates, such as woven and nonwoven fabrics and films, is well known. The printing of fabrics with inks and dyes is a common and widely used method for imparting patterns and colors to a basic fabric. Many current personal care products, such as diapers and training pants, include printed designs to improve their appearance. A problem with such printed products is that the printed design can be smeared or even removed during the handling the products encounter during manufacturing and packaging.

Another problem with these earlier printed products is that when they are wetted, the printed ink can run, fade, smear, and the like.

Yet another problem is that the crawling action of babies and small children subjects the exterior portion of the diaper and training pant to a high degree of abrasion. Such abrasion will quickly remove any printing which is not durably adhered to the outer surface of the product. Many of these products employ polyolefins in the manufacture of the component materials.

Generally speaking, color printing on cellulosic substrates such as cotton is well known in the art. Printing on polar polymers such as nylon and polyester is possible, but difficult compared to the same type of printing on cellulosic materials. More difficult than either of these substrates is the printing of non-polar polymers such as polyolefins. This is particularly true of fibrous polyolefin structures such as nonwoven webs, because current inks and dyes have limited adhesion to these non-polar inert materials.

Ink print adhesion to nonwoven polyolefin fibrous webs can be somewhat improved through the use of corona discharge treatment on the webs. However, this requires an additional step in the printing process along with higher energy costs and/or lower line speeds. In addition, if the corona discharge treatment is not carefully monitored, there is the possibility that the treatment will burn the nonwoven web, thereby increasing production costs due to the waste of damaged material.

The choice of ink or dye can create further problems. Standard dyes used in the fabric industry generally cannot be absorbed by the nonwoven fibers. Commercial inks currently used by the printing industry have poor adhesion to nonwoven fibrous webs, such as nonwoven polyolefin fibrous webs. Ink resin bases which have affinity to nonwoven fibrous webs, such as nonwoven polyolefin fibrous webs, generally do not have good printing characteristics that achieve high quality graphic reproduction, and require active solvents that attack the printing media. For example, high acetate content ink can have adverse effects on photopolymer printing plates and rubber printing plates used for flexographic printing. These adverse effects include plate swelling and premature plate failure.

In summary, problems with prior art printing include poor adhesion, poor printing characteristics, poor mechanical rub resistance, and poor chemical resistance of inks on dyes used to print nonwoven fibrous webs.

SUMMARY OF THE INVENTION

In one form of the invention there is provided a method of making an ink-printed nonwoven fibrous web comprising the steps of providing a continuously moving nonwoven fibrous web having a pair of opposed surfaces, printing an ink on one of the opposed surfaces to form an image thereon, and allowing the image to dry to yield an average wet crockfastness value of at least about 4 or greater.

In another form of the present invention there is provided an ink-printed nonwoven fibrous web comprising a nonwoven fibrous web having a pair of opposed surfaces, and an image printed with an ink on one of the surfaces; the nonwoven fibrous web having an average wet crockfastness value of at least about 4 or greater.

In still another form of the present invention there is provided a disposable absorbent article comprising a topsheet, a backsheet, and an absorbent composite between the topsheet and the backsheet. The backsheet comprises a nonwoven fibrous web having an inner surface facing toward the absorbent composite and an outer visible surface having an ink printed thereon. The nonwoven fibrous web has an average wet crockfastness value of at least about 4 or greater.

BRIEF DESCRIPTION OF THE DRAWINGS

The above-mentioned and other features and objects of this invention, and the manner of attaining them, will become more apparent and the invention itself will be better understood by reference to the following description of an embodiment of the invention taken in conjunction with the accompanying drawings, wherein.

DESCRIPTION OF A PREFERRED EMBODIMENT

Figure 1:
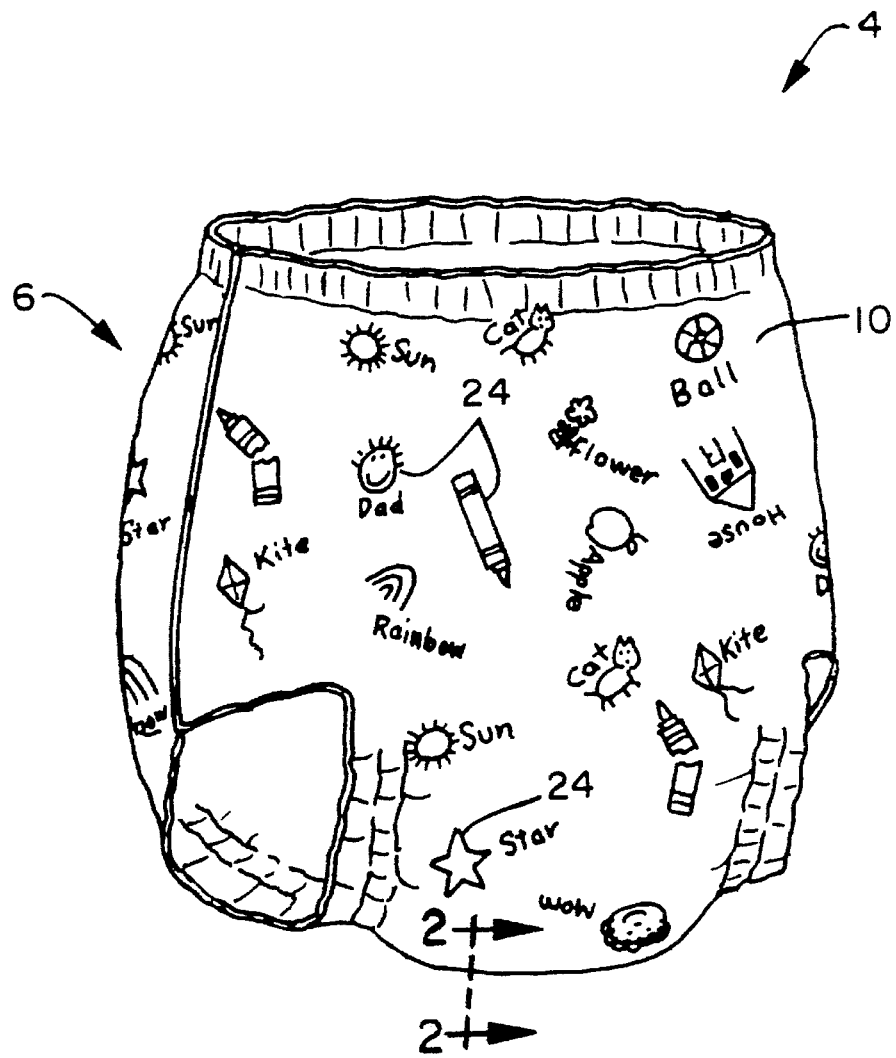
FIG. 1 is a perspective view of a disposable absorbent training pant incorporating the principles of the present invention.

The present invention utilizes a non-catalytic, block urethane-based ink applied desirably by a flexographic printing process to achieve a high strength mechanical bond to the nonwoven fibers. The urethane resins of this ink tolerate blends of solvent containing less than 100% esters or ketones. One desired blend contains N-propyl acetate, N-butyl acetate, and ethylene glycol monopropyl ether. The present invention reduces the adverse effects of active solvents on the printing media, and increases the wicking effect on the ink, allowing it to fill around the bond points and to coat the fibers of the nonwoven. This results in a better dyed cloth-like appearance, while retaining physical characteristics such as softness and drapability, as well as improving the mechanical bond strength, colorfastness, and crockfastness. To state this another way, the tactile properties of the printed web are substantially the same as the preprinted web. Crockfastness is a parameter that represents the degree of durability or adhesion of the ink to the web. Crockfastness is measured on a scale from 0 to 5, with 5 being the best or highest, and indicates the resistance of a material to the transfer of its color. Crockfastness and colorfastness will be discussed in greater detail hereafter.

Wicking, as used above, means to convey liquid by capillary action and wetting along the fiber surface. With the blend specified above, the ethylene glycol ether has very low surface tension, allowing it to flow along the outside of fibers. This results in a coating of the fibers and a filling around of the bond points.

Mechanical bond strength is the adherence by physical bonding to the surface of the nonwoven fibers, i.e., the urethane ink envelopes the fiber and forms a strong, flexible film that is resistant to rub-off, thereby resulting in good colorfastness and crockfastness.

In discussing inks, a "solvent-based" ink does not use water as the mobile phase to carry various resin(s) or binder(s), pigments, and additives, such as wax. Typically, "solvent-based" inks use one or more of various hydrocarbon solvents such as alcohols, esters, aliphatics, and aromatics to solubilize these components. Solvents that solubilize resins well are generally referred to as "active", while those that are not "active" are called "diluents". A "water-based" ink typically uses water predominantly as the mobile phase. Resins used with water-based inks typically are emulsions, and can be dispersions in some cases. Other solvents may be added to act as co-solvents or coalescing agents to help emulsions form a continuous film.

The present invention provides both a process and a material with an ink-printed nonwoven fibrous web exhibiting improved crockfastness. Although polyolefin fibers are desired from a cost-effective perspective in a competitive environment, other fibers can be used. These fibers are particularly useful in the manufacturing of personal care products, such as diapers, training pants, incontinence products, feminine products, and the like.

The ink-printed nonwoven fibrous webs of the present invention have improved abrasion resistance that reduces premature wear of the printed image on the nonwoven fabric and the transfer of the ink to other surfaces, while retaining desired physical characteristics such as softness and drapability.

The present invention further provides a printing process for personal care products that prints at high speeds on a continuously moving web to produce high volumes of printed product.

The term "image", when used with reference to printing, includes, but is not limited to, any type of design, mark, figure, identification codes, words, patterns, and the like.

The ink-printed nonwoven fibrous webs of the present invention can be adapted to a wide variety of other uses such as garments, workwear, cleanroom clothing, hospital gowns, and related supplies. Much of such clothing is very mundane in nature and research has indicated that people prefer wearing more colorful garments. Because such materials are made from nonwovens, generally it is not possible to create single or multicolor images without printing directly onto the surface of the nonwoven. When such printing is performed, it is important that the ink remain durably affixed to the nonwoven material.

The present invention further provides a process for printing with multi-color images requiring tight registration. Tight registration refers to the precise alignment of the different colors comprising an image. Inherent difficulties in achieving tight registration include the distance between the color printing stations, the uniformity of the printing substrate, and the extensibility of the printing substrate.

The present invention desirably utilizes flexographic printing to provide the proper balance of cost effective, high speed, high quality printing suitable for printing nonwoven fibrous webs, while maintaining the tactile softness of the web. Flexography is a printing technology which uses flexible raised rubber or photopolymer plates to carry the image to a given substrate. The flexible plates carry a typically low-viscosity ink directly onto the substrate. The quality of flexographic print in recent years has rapidly advanced such that, for many end-uses, it is comparable to lithographic or gravure printing. However, the traditional flexographic ink formulations have been limited in solvent choices due to plate incompatibilities that cause the plates to swell. The use of highly active solvents, such as aromatic hydrocarbons, ketones, or esters, cannot be used or must be drastically limited. These limitations, in the past, reduced the number of binder choices that are available when designing a crockfast ink system for polyolefin substrates. However, the non-catalytic, block urethane resin has demonstrated superior durability over traditional flexographic binders, such as styrene-maleic, rosin-maleic, acrylic solutions, or emulsions that either use water-alcohol, water-ammonia, or water-morpholine combinations. Although many of these binders may provide acceptable rub resistance to other substrates, like paper or filled films, they do not provide nonwoven fibrous webs with adequate crockfastness and colorfastness due predominantly to the inert nature of the polyolefin fiber. Even solvent-based inks that typically use aliphatic hydrocarbons with common binder types, such as polyamide, shellac, rosin esters, nitro-cellulose, and styrene-maleic, are not durable enough to provide the mechanical rub resistance needed for the end use.

The types of plates that can be used with the process of the present invention include plates identified as DuPont Cyrel® HL, PQS, HOS, PLS, and LP, which may be obtained from E. I. DuPont de Nemours & Co., Inc., 1007 Market Street, Wilmington, Del. 19898; a plate identified as BASF Nyloflex®, which may be obtained from BASF, 1255 Broad Street, Clifton, N.J. 07015; and a plate identified as Flexlight® type FL-SKOR®, which may be obtained from W.R. Grace & Co., 5210 Phillip Lee Drive, Atlanta, Ga. 303336. Others include laser etched vulcanized rubber cylinders, such as those supplied by Luminite Products Corporation, 115 Rochester Street, Salamanca, N.Y. 14779, or by Flexo Express, 270 Rochester Street, Salamanca, N.Y. 14779; or rubber printing plates, such as those supplied by Fulflex, Incorporated, P.O. Box 4549, Middleton, R.I. 02804. The rubber plates and vulcanized cylinder could be natural rubber, EPDM, nitrites, or urethanes.

In comparison to flexographic printing, screen printing equipment is relatively costly and cannot be run as fast as flexographic equipment.

Rotogravure printing uses an engraved print roll that increases the life of the print pattern and provides higher definition, but rotogravure entails higher cylinder costs and does not give consistent ink depositions on many nonwoven substrates. However, rotogravure equipment can be used with water-based, solvent-based, and hot-melt, adhesive-based inks.

Ink jet printing equipment generally requires inks that have a very low viscosity, often in the range of 1 to 10 centipoise, in order to achieve appropriate processing and application. Water-based and adhesive-based inks can be brought into this range. An advantage of ink jet printing equipment is the relatively high speed at which it can be run. Although only one color can be used per jet, multiple jets can be used to provide multiple colors.

The ability provided by the present invention to use an ink with very durable binders, such as a block polyurethane, has provided unique results in improving the visual and functional characteristics of the printed nonwoven fibrous webs, such as nonwoven polyolefin fibrous webs. The use of the desired solvent blend gives the ink a surface tension that is greatly reduced compared to water-based inks. This allows the ink to properly wet the high surface tension fibers, such as polyolefin fibers, for example. The enhanced fiber wicking provides improved ink distribution on fiber surfaces, on film-like bond point regions, and on fiber-fiber crossovers, so that more consistent print images are obtained.

In past printing processes, the ink would cover or print in a varying manner on bond points (i.e., those points where fibers cross and are bonded together), on the fibers themselves, and where the fibers merely cross, but are not bonded together. The varying ink printing or contrast is identified as a paler or more washed-out color, or even a change of color, due to the differences of surface characteristics between the bond points, fiber crossover regions, and the fibers themselves.

In accordance with the present invention, the wicking behavior of the applied ink inherently reduces the total ink concentration by providing an overall thin film which optimizes the crockfastness of a given system. This wicking behavior also provides better print definition that allows reproduction of fine detail and lines, and tighter print registration designs.

Desired solvent blends include blends ranging in volume up to about 50% of various acetates such as ethyl acetate, N-propyl acetate, isopropyl acetate, isobutyl acetate, N-butyl acetate, and blends thereof; up to about 10% of various alcohols including ethyl alcohol, isopropyl alcohol, normal propyl alcohol, and blends thereof; and up to 75% glycol ethers including Ektasolve® EP (ethylene glycol monopropyl ether), EB (ethylene glycol monobutyl ether), DM (diethylene glycol monomethyl ether), DP (diethylene glycol monopropyl ether), and PM (propylene glycol monomethyl ether), which can be obtained from Eastman Chemical, P.O. Box 431, Kingsport, Tenn. 37662. Other suitable solvents can also be obtained from Union Carbide Chemicals, 39 Old Ridgebury Road, Danbury, Conn. 06817. A desired solvent blend is a blend of about 50% to about 75% glycol ether, about 25% to about 35% N-propyl acetate, and about 15% to about 25% N-butyl acetate. Other glycols can be used such as DOWANOL®, obtainable from Dow Chemical, Midland, Mich. 48640.

The present invention utilizes higher pigment-to-binder ratios by weight than others previously described in water-based chemistries. The pigment-to-binder ratios of the present invention can range up to about 1:1.7. This higher pigment-to-binder ratio allows highly color-intense inks over the current water-based technologies that have a washed-out appearance.

The present invention also includes coloration in addition to the binders and solvent blends already described. Coloration can be imparted to these binders by the use of inert pigments and dyes, collectively referred to as pigments for purposes of the present invention, which can be added in levels of about 0.25% to about 40% on a dry weight basis.

The most common pigments include azo dyes (for example, Solvent Yellow 14, Dispersed Yellow 23, and Metanil Yellow), anthraquinone dyes (for example, Solvent Red 111, Dispersed Violet 1, Solvent Blue 56, and Solvent Orange 3), xanthene dyes (Solvent Green 4, Acid Red 52, Basic Red 1, and Solvent Orange 63), azine dyes (for example, Jet Black), and the like.

Major organic pigments include dairylide yellow AAOT (for example, Pigment Yellow 14 CI#21095), dairylide yellow AAOA (for example, Pigment Yellow 12 CI#21090), Phthalocyanine Blue (for example, Pigment Blue 15), lithol red (for example, Pigment Red 52:1 CI#15860:1), toluidine red (for example, Pigment Red 22 CI#12315), dioxazine violet (for example, Pigment Violet 23 CI#51319), phthalocyanine green (for example, Pigment Green 7 CI#74260), phthalocyanine blue (for example, Pigment Blue 15 CI#74160), naphthoic acid red (for example, Pigment Red 48:2 CI#15865:2).

Inorganic pigments include titanium dioxide (for example, Pigment White 6 CI#77891), carbon black (for example, Pigment Black 7 CI#77266), iron oxides (for example, red, yellow, and brown), ferric oxide black (for example, Pigment Black 11 CI#77499), chromium oxide (for example, green), ferric ammonium ferrocyanide (for example, blue), and the like.

Waxes are also included in the present invention to increase the slip and improve the rub-resistance of the inks of the printed polyolefin substrate. Common classifications of waxes include animal (for example, beeswax and lanolin), vegetable (for example, carnauba and candellilia), mineral (for example, paraffin and microcrystalline), and synthetic (for example, polyethylene, polyethylene glycol, and Teflon®). A recommended range is between about 0.5% to about 5% wax based on the total formula weight.

The printing provided by the present invention can be single color or multiple-color depending upon the aesthetic needs. Personal care products, such as diapers, feminine pads, adult incontinence garments, and training pants, typically have an outer cover which may include an external layer of nonwoven material. With many of these products, it is desirable to have one or more images in one or more colors printed on the product such that they are visible to the wearer. With training pants, for example, it is desirable to make the product as attractive and as fun as possible to wear in order to encourage the child to progress from training pants to underwear.

Figure 2:
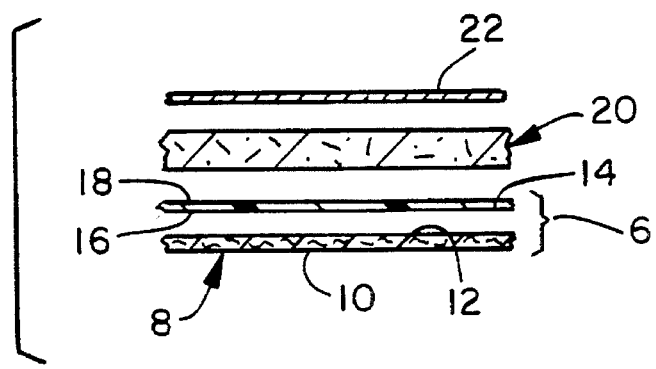
FIG. 2 is an exploded cross-sectional view of FIG. 1 taken along line 2—2 and viewed in the direction of the arrows.

One way to make these products more appealing is to print in bright colors a number of intricate, registered images on the outer visible surface of the backsheet or outer cover; by outer "visible" surface is meant that surface of the product that is visible when the product is worn. For example, in FIGS. 1–2, training pant 4 comprises a backsheet 6, which can be a two-layered laminate that includes a nonwoven polyolefin fibrous web 8 suitably joined to a liquid impervious film 14. Web 8 has opposed surfaces such as inner surface 12 and outer visible surface 10. Film 14 has opposed surfaces such as surface 16 that faces toward web inner surface 12 and surface 18 that faces toward absorbent composite 20. A liquid permeable topsheet 22 is positioned on the side of absorbent composite 20 opposite to backsheet 6, and is the layer that is against the skin of the wearer. It is outer visible surface 10 of nonwoven polyolefin fibrous web 8 that presents or forms the outermost, visible surface of training pant 4 and on which images 24 are printed.

Topsheet 22 can be made of any suitable liquid permeable material, and absorbent composite 20 can be made of any suitable absorbent materials appropriate for the intended use of the particular product. If desired, backsheet 6 can comprise only a liquid permeable layer, such as nonwoven polyolefin fibrous web 8, or can comprise a two-layered laminate as described above. More detailed descriptions of a training pant can be found in U.S. Pat. No. 4,940,464, filed Jul. 11, 1989, and U.S. Pat. application Ser. No. 043,132, filed on Mar. 25, 1993 now pending; both of which are assigned to the present assignee, and the contents of which are incorporated by reference herein.

In the past, it has been necessary to print these colored images on an underlying layer, such as a film layer, and then superimpose an outer layer, such as a nonwoven layer, over the top of the printed layer so that the colored images still can be viewed, albeit somewhat diffusely, through the nonwoven layer. For example, with reference to FIG. 2, images 24 (FIG. 1) would be printed on inner surface 12 of web 8, surface 16 of film 14, surface 18 of film 14, or another innermost surface, since current inks do not have the desired crockfastness. The present invention alleviates the need for such printing techniques, i.e., the need of an overlying outer layer, by providing an ink-printed nonwoven fibrous web that has high abrasion resistance measured by an average wet crockfastness value of at least about 4 or greater, and a desired average wet crockfastness value or rating of at least about 4.35 or greater.

As described, the present invention includes the block urethane ink and the nonwoven fibrous web onto which the ink is applied by a continuous web printing process. The term "continuous" means that the nonwoven fibrous web, such as a nonwoven polyolefin fibrous web, is delivered to be printed in a continuously moving manner, as is well known in the art of manufacturing disposable absorbent articles, such as diapers and training pants. Polyolefin-based webs include, but are not limited to, woven materials, nonwoven materials, knits, and films which employ polyolefin-based polymers. Examples of commonly employed polyolefins are polypropylene and polyethylene, including low density, high density, and linear low density polyethylene. It should be appreciated, however, that the present invention is not limited to these types of polyolefins, and embraces all types of polymers, copolymers, and natural fibers. In woven material applications, these materials can be made into continuous fibers, which are in turn woven into a fabric. In nonwoven applications, the fibers may be long, generally continuous fibers, such as spunbond and meltblown fibers, or they may be shorter staple length fibers, such as are commonly used in carded webs. Such polymers or copolymers may be extruded, cast, or blown into films for subsequent use according to the present invention. Other nonwovens suitable for use with the present invention include air laid, wet laid, solution spun fiber webs, and the like.

The fibers used in accordance with the present invention can be "straight" fibers in that they have the same general polymer or copolymer composition throughout. The fibers may also be multipolymer or multicomponent fibers, such as bicomponent fibers in which at least one component is a polyolefin, such as a polyethylene sheath and a polypropylene core fiber, or a polyethylene sheath and a polyester core fiber. In addition to sheath/core fiber configurations, other examples of suitable fiber cross-sections are side-by-side, sea-in-islands, and eccentric fiber configurations. Furthermore, fibers with non-circular cross-sections such as "Y" and "X" shapes may be used.

The fibers and/or webs may have other components and/or treatments. For example, adhesives, waxes, flow modifiers, processing aids and other additives may be used during the formation of the fibers and webs. In addition, pigments may be added to the fibers to change their color and other additives may be incorporated into the compositions to make the fibers and/or webs elastic. Lastly, blends of fibers, as well as straight and bicomponent fibers, may be combined to form nonwoven webs suitable for use with the present invention.

The web or substrate material can be used by itself, or in a multilayer configuration such as a laminate of one or more film and/or woven and/or nonwoven layers. Examples of such multilayer configurations include film/nonwoven laminates, or nonwoven/nonwoven laminates such as a spunbond/meltblown/spunbond three-layer laminates. By using such multilayer configurations, a variety of properties can be imparted to the laminate including breathability and/or liquid imperviousness.

When forming a nonwoven, such as a nonwoven polyolefin fibrous web or substrate, the fiber size and basis weight of the material can be varied according to the particular end use. In personal care product and medical fabric usage, typical fiber sizes will range from between about 0.1 to about 10 denier, and basis weights will range from between about 10 grams per square meter to about 105 grams per square meter. For other applications, both the fiber size and the basis weight can be adjusted.

To achieve sufficient abrasion resistance and durability, testing has indicated that the ink, once applied and allowed to dry, should yield an average wet crockfastness value of at least about 4 or greater. With reference to the present invention, colorfastness is the resistance of a material to change in any of its color characteristics, to the transfer of its colorant(s) to adjacent materials, or both, as a result of the exposure of the material to any environment that might be encountered during the processing, testing, storage, or use of the material. The terms crocking, crock, and crockfastness specifically relate to the transfer of color principally by a rubbing action from the surface of a colored fabric to an adjacent area of the same fabric or to another surface. Testing for wet crockfastness is a method for determining whether or not, and to what degree, a color may be transferred from the surface of the printed material to other surfaces by rubbing. As a result, crockfastness is a means for gauging the abrasion resistance of an ink once it has been printed onto a web or substrate, such as a nonwoven polyolefin fibrous web or substrate. This test is set forth in detail below, but suffice it to say that testing has shown that conventional inks used in flexography, when applied to nonwoven polyolefin fibrous webs or substrates, only exhibit crockfastness ratings in the range of about 1 to about 3, and such inks when covered with a clear overlacquer only increased their crockfastness ratings up to about 3.

In contrast, the inks of the present invention generally yield average wet crockfastness ratings of at least about 4 or greater on a scale of 1 to 5. Thus, a desired feature of the present invention is that the inks, when applied to a nonwoven fibrous web or substrate, such as a nonwoven polyolefin fibrous web or substrate, have an average wet crockfastness value of at least about 4 or greater, and a desired average wet crockfastness value of at least about 4.35 or greater.

Having described the materials and equipment suitable for use with the present invention, a series of inks were prepared and then printed onto nonwoven polyolefin fibrous webs, in this case a spunbond polypropylene web having a basis weight between about 23 grams per square meter to about 31 grams per square meter. A wet crock test method was used to measure whether these combinations of inks and polyolefin-based nonwovens had sufficient abrasion resistance. The wet crock test method was based upon American Association of Textile Chemists and Colorists (AATCC) Test Method 116–1983, which is incorporated herein in its entirety with two modifications. The test method consisted of essentially rubbing a 2"×2" square cotton test swatch against the wet material of interest for a specific number of turns, while maintaining a constant pressure supplied by a standard weight (40 ounces). According to the test procedure, the test specimens were then analyzed for the CIELAB color difference which is expressed as $\Delta E$. The $\Delta E$ was then converted to a number between 1 and 5 using the following equation: C.R. =A exp. (–B) where A=5.063244 and B=0.059532 ($\Delta E$) if $\Delta E$ is less than 12, or A=4.0561216 and B=0.041218 ($\Delta E$) if $\Delta E$ is greater than 12. This number C.R. is the crockfastness rating. A rating of 1 corresponds to a low or bad result, while a rating of 5 is the highest possible test result, and this value would indicate that essentially no color was rubbed off the sample material.

AATCC Test Method 116-1983 was modified in the following manner. In the official test, a 20 turn rubbing procedure is standard, however, under the modified test method used herein, a 5 turn rubbing procedure was used. The 5 turns were used because the test specimens of the present invention cannot generally endure the severe abrasion incurred during a 20 rub procedure given the 40 ounce loading, as indicated by the fibers roping and/or holes appearing in the material when nonwoven webs are being tested. Thus, the 5 turn rubbing procedure represented a more reasonable abrasion of the materials during usage, as would typically be encountered if a printed, polyolefin-based nonwoven web was used as a medical fabric or a backsheet on a personal care product, such as a diaper or training pant.

The second change in the test for use with the present invention was that the amount of color transferred to the test specimen was measured using a Hunter Colorimeter and/or an X-Rite Spectrodensitometer, instead of the AATCC Chromatic Transference Scale or grade scale measuring device. With the Colorimeter or Spectrodensitometer, greater objectivity in evaluating the results was possible due to less operator dependence, and it was also possible to achieve higher efficiency and consistency for on-line quality assurance. The Hunter Colorimeter Model D25 is manufactured by Hunter Associates Laboratory, Inc., of Reston, Va. The X-Rite 938 Spectrodensitometer is manufactured by X-Rite, Inc., of Grandville, Mich. The crock test was performed using AATCC crock meter Model CM-6 supplied by Atlas Electric Device Company of Chicago, Ill.

EQUIPMENT AND MATERIALS USED

1. Rotary Vertical Crockmeter—sharp edges on the vertical rod were filed to reduce abrasion of nonwoven materials.

2. Crockmeter cloth, standard 2×2 inches (51 mm) test squares.

3. Hunter Colorimeter Model D25 manufactured by Hunter Associates Laboratory, Inc., of Reston, Va., or an X-Rite Spectrodensitometer manufactured by X-Rite, Inc., of Grandville, Mich.

4. Apple Juice—Gerber brand Baby's 1st Foods® apple juice from freshly pressed apples.

5. Distilled water—locally purchased (Pick-N-Save Grocery Store, Neenah, Wis.) Roundy's brand steam distilled water.

6. Saline solution—S/P Certified Blood Bank Saline, Catalogue No. B3158-1, 8.5 grams sodium chloride per liter of reagent grade water.

7. Paper Cutter, standard 12×12 inches (305×305 mm) minimum cutting area, obtained from Testing Machines, Inc., Amityville, N.Y.

8. Balance, readable to 0.01 gram (Mettler PE 1600).

9. Room with standard-conditions atmosphere: temperature=23±1° C. (73.4±1.8° F.) and relative humidity=50±2 percent. Testing outside the specified limits for temperature and humidity may not yield valid results.

SPECIAL INSTRUCTIONS

Repair accidental damage or wear of the abrasive paper, rubbing finger or crock cloth spring clip as follows: neatly renew the abrasive paper; resurface the finger by movement on an extra piece of abrasive paper in a manner simulating regular use, and bend the clip further open or shut, over an inserted rod of the proper diameter, as required.

SPECIMEN PREPARATION

The test specimen was a spunbond polypropylene web having a basis weight between about 23 gsm to about 31 gsm. The test specimens were cut approximately 2-¼×2-¼ inches (57×57 mm) with the test area centered on the square.

TESTING PROCEDURE

1. Weigh the Crockmeter cloth standard. Record the weight.

2. Thoroughly wet out the material with the appropriate solution.

3. Bring the wet pick-up to 65±5 percent (This is done by wringing or blotting the excess solution from the material, weighing the material and calculating the percent pick-up. Calculate: wet weight minus dry weight divided by dry weight times 100=percent pick-up). To prevent evaporation, prepare one wet cloth at a time for testing.

4. Tilt the upper half of the machine away to allow access to the base of the machine. Place a test square of the Crockmeter cloth on the end of the vertical rod and fasten it with the spring clip.

5. Hold the test specimen on the machine base at the point the vertical rod contacts the base. Tilt the upper half of the machine back to the operating position with the test square at the end of the shaft in contact with the test specimen. Place the weight on the vertical shaft to give a 40 ounce (1134 grams) pressure on the test square.

6. With the left hand, hold the test specimen in position on the base. Turn the crank five turns with the right hand. This produces about 10 reciprocal turns of the vertical shaft.

7. Tilt the upper part of the machine back and remove the test specimen and test square.

8. Allow the test specimen to air dry before grading.

EVALUATION

The next step is the second modification to the AATCC test procedure, as earlier described above. The second modification is that the amount of color transferred to the test specimen was measured using a Hunter Colorimeter and/or an X-Rite Spectrodensitometer, instead of the AATCC Chromatic Transference Scale or a grade scale measuring device. As earlier described, $\Delta E$ is then obtained and converted to a crockfastness rating between 1 and 5 using the equation set forth above.

In order to demonstrate the abrasion resistance of the materials according to the present invention, two sets of testing were performed, and are labeled Wet Crocking Results I and Wet Crocking Results II. Three different types of liquid were used in each of the two sets of testing; those three liquids were apple juice, distilled water, and saline solution, as described above. In each of the two sets of testing, each of the three liquids were tested with 12 different ink formulations. For example, under Wet Crocking Results I, Apple Juice, Test 1 represents a specific ink formulation that was tested utilizing the wet crock test method earlier described, and which yielded an average wet crockfastness rating or value of 3.66. Each specific ink formulation was tested ten times with ten test specimens. The average was determined by individually calculating the crockfastness rating for each of the 10 test specimens, summing the 10 crockfastness ratings, and then dividing by 10 to get the average wet crockfastness rating.

Various colors were tested with different ink formulations. Each color was created by mixing an appropriate amount of pigment with the ink so as to result in the desired color. Each color is identified with a Pantone color target code as follows:

| Colors | Codes |
|---|---|
| Aqua | PMS 3252 |
| Lavender | PMS 2562 |
| Light Yellow | PMS 1215 |
| Pink | PMS 210 |
| Peach | PMS 169 |
| Blue | PMS 279 |
| Green | PMS 3272 |
| Red | PMS 191 |
| Yellow | PMS 115 |

The ink formulations were as follows:

(A) For Tests 1–4, 13–16, and 25–28, which are comparative examples, the ink formulation was comprised of an acrylic emulsion in a pigment-to-binder ratio of about 17:83; the raw ink's viscosity was reduced by the addition of a blend of 90% by volume of water and 10% by volume ethylene glycol monopropyl ether to a final viscosity of about 25 seconds using a Zahn #2 cup viscometer. This ink formulation can be purchased from Findley Adhesives, Inc., of Wauwatosa, Wis., and is identified as L7064.

For Tests 37–40, 49–52, and 61–64, which also are comparative examples, the ink formulation was comprised of an ethylene vinyl acetate emulsion in a pigment-to-binder ratio of about 17:83; the raw ink's viscosity was reduced by the addition of 100% by volume of water to a final viscosity of about 25 seconds using a Zahn #2 cup viscometer. This ink formulation can be purchased from Findley Adhesives, Inc., of Wauwatosa, Wis., and is identified as L8305.

(B) For Tests 5–8, 17–20, 29–32, 41–44, 53–56, and 65–68, which are comparative examples, the ink formulation was comprised of a modified nitrocellulose solution in a pigment-to-binder ratio of about 17:83;, the raw ink's viscosity was reduced by the addition of a blend of 80% by volume of ethyl alcohol and 20% by volume of N-propyl acetate to a final viscosity of about 25 seconds using a Zahn #2 cup viscometer. This ink formulation is identified by the trade name Multibond and can be purchased from Sun Chemical Company, Fort Lee, N.J.

(C) For Tests 9–12, 21–24, 33–36, 45–48, 57–60, and 69–72, which are examples of the present invention, an ink formulation purchased from Sun Chemical Company, Fort Lee, N.J., under the tradename Parabond was used in accordance with the principles of the present invention. The ink's viscosity was reduced by the addition of a blend of 75% by volume of ethylene glycol monopropyl ether and 25% by volume of N-propyl acetate to a final viscosity of about 25 seconds using a Zahn #2 cup viscometer.

| Ink | Color | Crockfastness avg. | std. dev. |
|---|---|---|---|
| *Wet Crocking Results I* | | | |
| *Apple Juice* | | | |
| Test 1 | Aqua | 3.66 | 0.36 |
| Test 2 | Lavender | 2.91 | 0.59 |
| Test 3 | Light Yellow | 4.15 | 0.25 |
| Test 4 | Pink | 3.19 | 0.18 |
| Test 5 | Aqua | 1.94 | 0.30 |
| Test 6 | Lavender | 2.44 | 0.22 |
| Test 7 | Peach | 1.91 | 0.22 |
| Test 8 | Pink | 1.80 | 0.18 |
| Test 9 | Aqua | 4.35 | 0.11 |
| Test 10 | Lavender | 4.54 | 0.16 |
| Test 11 | Light Yellow | 4.40 | 0.22 |
| Test 12 | Pink | 4.40 | 0.25 |
| *Distilled Water* | | | |
| Test 13 | Aqua | 3.60 | 0.27 |
| Test 14 | Lavender | 2.96 | 0.31 |
| Test 15 | Light Yellow | 4.23 | 0.26 |
| Test 16 | Pink | 3.02 | 0.47 |
| Test 17 | Aqua | 1.82 | 0.22 |
| Test 18 | Lavender | 2.30 | 0.10 |
| Test 19 | Peach | 1.93 | 0.25 |
| Test 20 | Pink | 1.83 | 0.24 |
| Test 21 | Aqua | 4148 | 0.12 |
| Test 22 | Lavender | 4.51 | 0.08 |
| Test 23 | Light Yellow | 4.67 | 0.13 |
| Test 24 | Pink | 4.61 | 0.61 |
| *Saline Solution* | | | |
| Test 25 | Aqua | 3.46 | 0.25 |
| Test 26 | Lavender | 2.96 | 0.24 |
| Test 27 | Light Yellow | 4.26 | 0.31 |
| Test 28 | Pink | 3.41 | 0.28 |
| Test 29 | Aqua | 1.80 | 0.18 |
| Test 30 | Lavender | 2.53 | 0.23 |
| Test 31 | Peach | 1.86 | 0.28 |
| Test 32 | Pink | 1.87 | 0.20 |
| Test 33 | Aqua | 4.48 | 0.09 |
| Test 34 | Lavender | 4.45 | 0.19 |
| Test 35 | Light Yellow | 4.75 | 0.08 |
| Test 36 | Pink | 4.68 | 0.06 |
| *Wet Crocking Results II* | | | |
| *Apple Juice* | | | |
| Test 37 | Blue | 1.42 | 0.11 |
| Test 38 | Green | 2.74 | 0.49 |
| Test 39 | Red | 2.24 | 0.24 |
| Test 40 | Yellow | 1.55 | 0.27 |
| Test 41 | Blue | 2.30 | 0.36 |
| Test 42 | Green | 2.92 | 0.54 |
| Test 43 | Red | 1.70 | 0.28 |
| Test 44 | Yellow | 2.61 | 0.40 |
| Test 45 | Blue | 4.07 | 0.21 |
| Test 46 | Green | 4.01 | 0.17 |
| Test 47 | Red | 3.17 | 0.25 |
| Test 48 | Yellow | 4.13 | 0.19 |
| *Distilled Water* | | | |
| Test 49 | Blue | 1.78 | 0.35 |
| Test 50 | Green | 3.19 | 0.52 |
| Test 51 | Red | 274 | 0.45 |
| Test 52 | Yellow | 1.90 | 0.29 |
| Test 53 | Blue | 2.41 | 0.53 |
| Test 54 | Green | 2.77 | 0.27 |
| Test 55 | Red | 1.65 | 0.34 |
| Test 56 | Yellow | 2.62 | 0.44 |
| Test 57 | Blue | 4.15 | 0.16 |
| Test 58 | Green | 4.30 | 0.16 |
| Test 59 | Red | 4.00 | 0.15 |
| Test 60 | Yellow | 4.66 | 0.13 |
| *Saline Solution* | | | |
| Test 61 | Blue | 1.82 | 0.25 |
| Test 62 | Green | 3.00 | 0.25 |
| Test 63 | Red | 2.40 | 0.21 |
| Test 64 | Yellow | 2.01 | 0.44 |
| Test 65 | Blue | 2.51 | 0.27 |
| Test 66 | Green | 2.81 | 0.49 |
| Test 67 | Red | 1.63 | 0.38 |
| Test 68 | Yellow | 2.75 | 0.33 |

-continued

| Ink | Color | Crockfastness avg. | std. dev. |
|---|---|---|---|
| Test 69 | Blue | 4.25 | 0.18 |
| Test 70 | Green | 4.32 | 0.28 |
| Test 71 | Red | 4.12 | 0.36 |
| Test 72 | Yellow | 4.58 | 0.17 |

While this invention has been described as having a preferred embodiment, it will be understood that it is capable of further modifications. This application is thereby intended to cover any variations, equivalents, uses, or adaptations of the invention following the general principles thereof, and including such departures from the present disclosure as come or may come within known or customary practice in the art to which this invention pertains and fall within the limits of the appended claims.

What is claimed is:

1. A method of making an ink-printed nonwoven fibrous web, comprising the steps of:
   providing a continuously moving nonwoven fibrous web comprising a pair of opposed surfaces,
   printing an ink on one of the opposed surfaces to form an image thereon, and
   allowing the image to dry to yield an average wet crockfastness value of at least about 4 or greater.

2. The method of claim 1 wherein the step of printing is flexographic printing.

3. The method of claim 1 wherein the step of printing is rotogravure printing.

4. The method of claim 1 wherein the step of printing is ink-jet printing.

5. The method of claim 1 wherein the ink comprises a non-catalytic block urethane resin, and a solvent blend comprising up to about 50% by volume of acetate and up to about 75% by volume of glycol ether.

6. The method of claim 5 wherein the acetate is selected from the group consisting of ethyl acetate, N-propyl acetate, N-butyl acetate, isopropyl acetate, isobutyl acetate, butyl acetate, and blends thereof.

7. The method of claim 5 wherein the solvent blend further comprises up to about 10% by volume of alcohol.

8. The method of claim 5 wherein the glycol ether is selected from the group consisting of ethylene glycol monopropyl ether, ethylene glycol monobutyl ether, diethylene glycol monomethyl ether, diethylene glycol monopropyl ether, propylene glycol monomethyl ether, and blends thereof.

9. The method of claim 7 wherein the alcohol is selected from the group consisting of ethyl alcohol, isopropyl alcohol, N-propyl alcohol, and blends thereof.

10. The method of claim 1 wherein the nonwoven fibrous web has a basis weight between about 10 grams per square meter to about 105 grams per square meter.

11. The method of claim 10 wherein the nonwoven fibrous web comprises polyolefin fibers.

12. The method of claim 1 wherein the step of printing includes printing with inks of different colors.

13. An ink-printed nonwoven fibrous web, comprising:
    a nonwoven fibrous web comprising a pair of opposed surfaces, and
    an image printed with an ink on one of said surfaces,
    said nonwoven fibrous web having an average wet crockfastness value of at least about 4 or greater.

14. The web of claim 13 wherein said ink comprises a non-catalytic block urethane resin, and a solvent blend comprising up to about 50% by volume of acetate and up to about 75% by volume of glycol ether.

15. The web of claim 14 wherein said acetate is selected from the group consisting of ethyl acetate, N-propyl acetate, N-butyl acetate, isopropyl acetate, isobutyl acetate, butyl acetate, and blends thereof.

16. The web of claim 14 wherein said solvent blend further comprises up to about 10% by volume of alcohol.

17. The web of claim 14 wherein said glycol ether is selected from the group consisting of ethylene glycol monopropyl ether, ethylene glycol monobutyl ether, diethylene glycol monomethyl ether, diethylene glycol monopropyl ether, propylene glycol monomethyl ether, and blends thereof.

18. The web of claim 16 wherein said alcohol is selected from the group consisting of ethyl alcohol, isopropyl alcohol, N-propyl alcohol, and blends thereof.

19. The web of claim 13 wherein said web has a basis weight between about 10 grams per square meter to about 105 grams per square meter.

20. The web of claim 13 wherein said nonwoven fibrous web comprises polyolefin fibers.

21. A disposable absorbent article, comprising:
    a topsheet, a backsheet, and an absorbent composite between said topsheet and said backsheet,
    said backsheet comprising a nonwoven fibrous web having an inner surface facing toward said absorbent composite and an outer visible surface,
    said outer visible surface having an ink printed thereon,
    said nonwoven fibrous web having an average wet crockfastness value of at least about 4 or greater.

22. The article of claim 21 wherein said ink comprises a non-catalytic block urethane resin, and a solvent blend comprising up to about 50% by volume of acetate and up to about 75% by volume of glycol ether.

23. The article of claim 22 wherein said acetate is selected from the group consisting of ethyl acetate, N-propyl acetate, N-butyl acetate, isopropyl acetate, isobutyl acetate, butyl acetate, and blends thereof.

24. The article of claim 22 wherein said solvent blend further comprises up to about 10% by volume of alcohol.

25. The article of claim 22 wherein said glycol ether is selected from the group consisting of ethylene glycol monopropyl ether, ethylene glycol monobutyl ether, diethylene glycol monomethyl ether, diethylene glycol monopropyl ether, propylene glycol monomethyl ether, and blends thereof.

26. The article of claim 24 wherein said alcohol is selected from the group consisting of ethyl alcohol, isopropyl alcohol, N-propyl alcohol, and blends thereof.

27. The article of claim 21 wherein said web has a basis weight between about 10 grams per square meter to about 105 grams per square meter.

28. The article of claim 27 wherein said web comprises polyolefin fibers.

\* \* \* \* \*